United States Patent
Schmenger et al.

(10) Patent No.: US 7,637,962 B2
(45) Date of Patent: Dec. 29, 2009

(54) MULTICOMPONENT KIT AND METHOD FOR DYEING KERATIN FIBERS

(75) Inventors: Juergen Schmenger, Weiterstadt (DE); Petra Braun, Muenster (DE)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 11/572,721

(22) PCT Filed: May 18, 2005

(86) PCT No.: PCT/EP2005/005400

§ 371 (c)(1),
(2), (4) Date: Apr. 23, 2008

(87) PCT Pub. No.: WO2006/012935

PCT Pub. Date: Feb. 9, 2006

(65) Prior Publication Data

US 2008/0263786 A1    Oct. 30, 2008

(30) Foreign Application Priority Data

Jul. 30, 2004  (DE) ................... 10 2004 037 105

(51) Int. Cl.
*A61Q 5/10* (2006.01)
(52) U.S. Cl. .................. 8/405; 8/406; 8/435; 8/526; 132/202; 132/208
(58) Field of Classification Search ........... 8/405, 8/406, 435, 526; 132/202, 208
See application file for complete search history.

(56) References Cited

U.S. PATENT DOCUMENTS

| 3,960,476 A | 6/1976 | Ghilardi et al. |
| 4,566,875 A | 1/1986 | Grollier et al. |
| 5,261,926 A | 11/1993 | Lang et al. |
| 5,560,750 A | 10/1996 | Crews et al. |
| 6,440,175 B1 | 8/2002 | Stanley, III |

(Continued)

FOREIGN PATENT DOCUMENTS

DE            2 005 076        8/1970

(Continued)

OTHER PUBLICATIONS

E. Sagarin: "Cosmetics, Science and Technology" Interscience Publishers Inc., New York, 1957 pp. 503-507. (in English).

(Continued)

*Primary Examiner*—Eisa B Elhilo
(74) *Attorney, Agent, or Firm*—Michael J. Striker

(57) ABSTRACT

The present application relates to a multicomponent kit for dyeing keratin fibers which consists of
(i) a dye carrier mass (A) which is free from dyes and dye precursors;
(ii) a granular composition (B) which comprises at least one oxidation dye precursor and/or at least one direct dye and optionally at least one keratin-lightening or bleaching substance; and optionally
(iii) a suitable oxidizing agent (C);
to a method for dyeing keratin fibers and to the use of a combination of a dye-free dye carrier mass (A) and a granular dye-containing and optionally bleaching-agent-containing composition (B) and optionally an oxidizing agent (C) for the individual preparation of colorants for keratin fibers directly prior to dyeing or bleaching the keratin fibers.

9 Claims, 2 Drawing Sheets

U.S. PATENT DOCUMENTS 6,673,123 B2 * 1/2004 Schulze zur Wiesche et al. ............................ 8/405

FOREIGN PATENT DOCUMENTS

| DE | 1 617 826 | 3/1972 |
| DE | 42 33 874 | 4/1994 |
| DE | 195 48 291 | 6/1997 |
| DE | 102 30 414 | 9/2003 |
| DE | 102 60 880 | 7/2004 |
| EP | 0 148 681 | 7/1985 |
| EP | 1 426 037 | 6/2004 |
| GB | 1 144 100 | 3/1969 |
| GB | 1 288 128 | 9/1972 |

OTHER PUBLICATIONS

H. Janistyn: "Handbuch Der Kosmetika Und Riechstoffe", vol. 3, 1973, pp. 388-397.

K. Schrader: "Grundlagen Und Rezepturen Der Kosmetika" 2-nd Edition, 1989, pp. 782-814.

Jerry March: "Advances Organic Chemistry-Reactions, Mechanisms and Structure", 5-th Edition, 2001, pp. 368-375. (in English).

* cited by examiner

US 7,637,962 B2

MULTICOMPONENT KIT AND METHOD FOR DYEING KERATIN FIBERS

CROSS-REFERENCE TO RELATED APPLICATIONS

This application is the national stage entry of PCT/EP2005/005400, filed 18 May 2005 and claims priority under 35 U.S.C. 119(a)-(d) to German Patent Application Number DE 1020040371059, fled 30 Jul. 2004.

BACKGROUND OF THE INVENTION

1. Field of the invention

The present invention relates to a multicomponent kit and to a method for dyeing keratin fibers, in particular human hair.

2. Description of Related Art

Dyes which are usually used for dyeing keratin fibers are so-called direct dyes, nitro dyes and pigment dyes or oxidation dyes which are in the form of colorless developer/coupler precursors.

Colorants produced by the prior art are supplied in customary administration forms. These administration forms vary from liquid to cream-like and wax-type products. Aerosols, for example so-called mousse hair colors, are also used. According to the prior art, pulverulent colors are likewise on the market which have to be mixed with an aqueous medium prior to use. Examples of pulverulent colorants are known, for example, from the patent specification U.S. Pat. No. 3,960,476 or the patent specification U.S. Pat. No. 6,440,175.

The stated colorants according to the prior art are usually nuanced in a ready-to-use form. This has the disadvantage that, on the one hand, a large number of nuances has to be kept in supply, which leads inter alia to high storage costs, and, on the other hand, the creation of individual or particular nuances is only possible with difficulty.

BRIEF SUMMARY OF THE INVENTION

Surprisingly, it has now been found that this problem can be solved through the use of a special multicomponent kit and/or a special method.

Since the multicomponent kit according to the invention comprises the dye or the dyes and/or the oxidizing agent in granule form, which have been created and are constructed in terms of color according to the color circle, the trained person skilled in the art is able, while taking into consideration certain reactionkinetic dye developments from a manageable number of dye premixtures, to create an individual color nuance tailored in each case to the wishes of the customer which, in addition, produces a more intense color than standard commercial colorants.

DETAILED DESCRIPTION OF THE INVENTION

Figure 1:
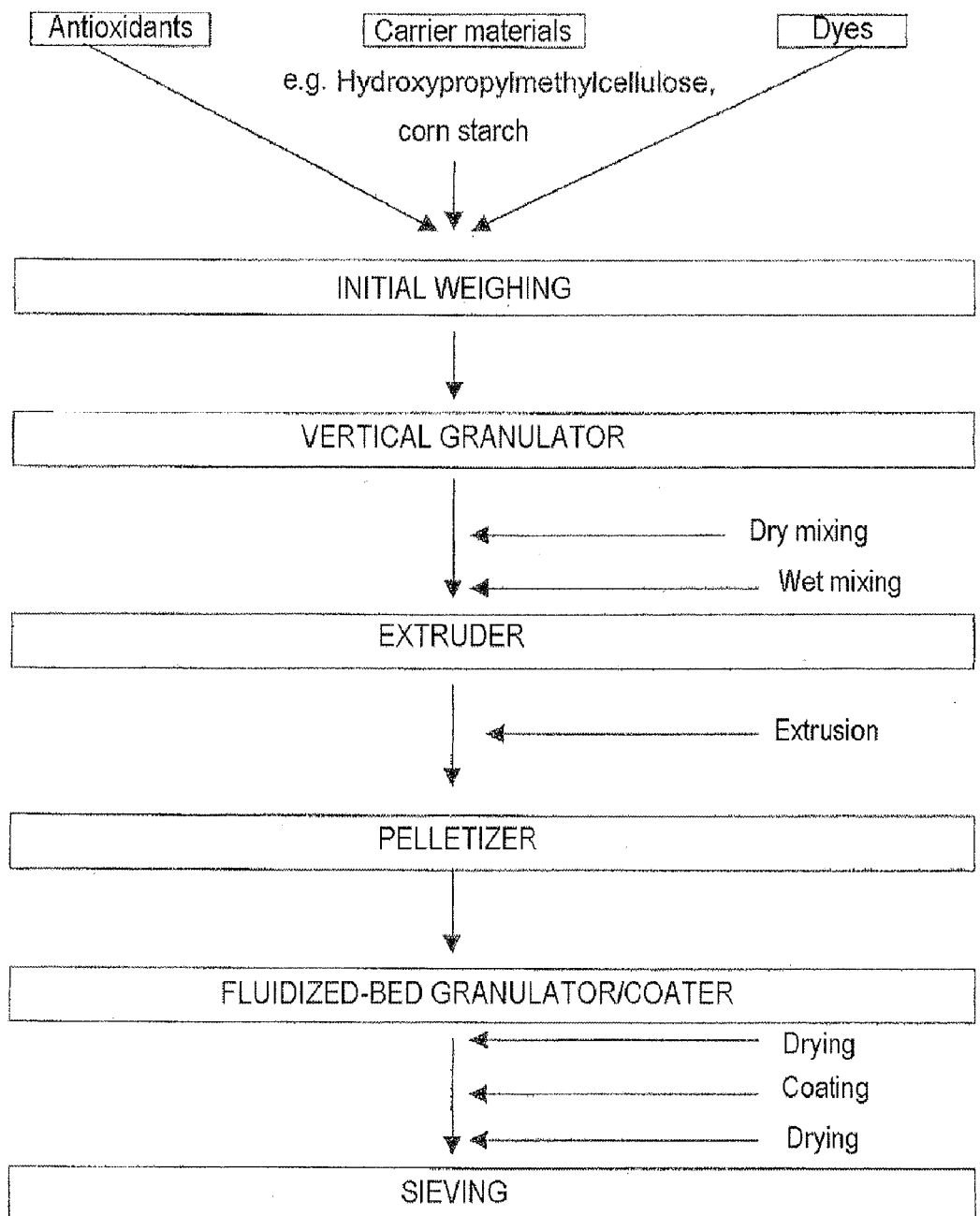
FIG. 1 is a flow chart illustrating a method of producing dye pellets by means of extrusion technology.

The present invention therefore provides a multicomponent kit for dyeing keratin fibers, in particular human hair, which is characterized in that it consists of the following components:

(i) a dye carrier mass (A) which is free from dyes and dye precursors (e.g. a dye-free liquid color mass, cream gel color mass or cream color mass);
(ii) a granular composition (B) which comprises at least one oxidation dye precursor and/or at least one direct dye and optionally at least one keratin-lightening or bleaching substance; and optionally
(iii) a suitable oxidizing agent (C).

The present invention further provides the use of a combination of a dye-free dye carrier mass (A) and a granular dye-containing and optionally bleaching-agent-containing composition (B) and optionally an oxidizing agent (C) for the individual preparation of colorants for keratin fibers—in particular human hair—directly prior to dyeing the keratin fibers.

Furthermore, the present invention relates to a method for dyeing or simultaneously dyeing and lightening keratin fibers—in particular human hair—in which a mixture of the above described compositions (A) and (B) and optionally (C) prepared individually directly prior to use is applied to the keratin fibers.

The compositions (A), (B) and (C) are preferably used in the following amounts:
Component (A): 10 to 120 g, in particular 20 to 80 g;
Component (B): 0.1 to 20 g, in particular 0.5 to 12 g;
Component (C): 10 to 120 g, in particular 20 to 80 g;

The ratio of (A) to (B) is generally 1000:1 to 2:1, preferably 200:1 to 4:1 and in particular 100:1 to 5:1.

The ratio of (C) to (A) is generally 3:1 to 1:3, preferably 1:1.

Suitable oxidation dye precursors which may be used in the composition (B) are, for example, the following developer substances and coupler substances and selfcoupling compounds:

(i) Developer substances: 1,4-diaminobenzene (p-phenylenediamine), 1,4-diamino-2-methylbenzene (p-tolylenediamine), 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 2-(2-(acetylamino)ethoxy)-1,4-diaminobenzene, 4-phenylaminoaniline, 4-dimethylaminoaniline, 4-diethylaminoaniline, 4-dipropylaminoaniline, 4-[ethyl(2-hydroxyethyl)amino]aniline, 4-[di(2-hydroxyethyl)amino]aniline, 4-[di(2-hydroxyethyl)amino]-2-methylaniline, 4-[(2-methoxyethyl)amino]aniline, 4-[(3-hydroxypropyl)amino]aniline, 4-[(2,3-dihydroxypropyl)amino]aniline, 1,4-diamino-2-(2-hydroxyethyl)benzene, 1,4-diamino-2-(1-methylethyl)benzene, 1,3-bis[(4-aminophenyl)(2-hydroxyethyl)amino]-2-propanol, 1,4-bis[(4-aminophenyl)amino]butane, 1,8-bis(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4- methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methylphenol, alone or in a mixture with one another.

(ii) Coupler substances: N-(3-dimethylaminophenyl)urea, 2,6-diaminopyridine, 2-amino-4-[(2-hydroxyethyl)amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole, 2,3-indolenedione, alone or in a mixture with one another.

(iii) Self-coupling compounds: 2-amino-5-methylphenol, 2-amino-6-methylphenol, 2-amino-5-ethoxyphenol or 2-propylamino-5-aminopyridine.

Among the abovementioned oxidation dyes, the following compounds, alone or in combination with one another, are particularly preferred: 2,5-diaminotoluene, 2,4-diaminophenoxyethanol, resorcinol, 2-methylresorcinol, m-aminophenyl, 4-amino-m-kresol, 4-amino-2-hydroxytoluene, 6-amino-m-kresol, 2-amino-4-hydroxyethylaminoanisole, 1-naphthol, hydroxyethyl-3,4-methylenedioxyaniline, 2,5-diaminophenyl ethanol, N,N-bis(2-hydroxyethyl)-p-phenylenediamine, phenylmethylpyrazolone, 1-hydroxyethyl-4,5-diaminopyrazole and 2-amino-6-chloro-4-nitrophenol or salts thereof.

The total amount of oxidation dye precursors present in the composition (B) according to the invention is about 0.1 to 70% by weight, in particular about 0.5 to 50% by weight.

In addition, to achieve certain color nuances, customary natural and/or synthetic direct dyes, for example so-called plant dyes such as henna or indigo, triphenylmethane dyes, aromatic nitro dyes, azo dyes, quinone dyes, cationic or anionic dyes, may also be added.

However, it is also possible for the composition (B) according to the invention to comprise exclusively direct dyes.

Suitable synthetic dyes which may be mentioned are, for example: hydroxyethyl-2-nitro-p-toluidine, 2-hydroxyethylpicramic acid, 4-nitrophenylaminourea, tri(4-amino-3-methylphenyl)carbenium chloride (Basic Violet 2), 1,4-diamino-9,10-antracenedione (Disperse Violet 1), 1,4-bis[(2-hydroxyethyl)amino]-2-nitrobenzene, 1-(2-hydroxyethyl)amino-2-nitro-4-[di(2-hydroxyethyl)amino]benzene (HC Blue No. 2), 1-amino-3-methyl-4-[(2-hydroxyethyl)amino]-6-nitrobenzene (HC Violet No. 1), 4-[ethyl(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxypropyl)amino]-4-[methyl(2-hydroxyethyl)amino]-2-nitrobenzene (HC Blue No. 10), 1-[(2,3-dihydroxypropyl)amino]-4-[ethyl(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl(2,3-dihydroxypropyl)amino]-2-nitrobenzene (HC Blue No. 6), 2-((4-amino-2-nitrophenyl)amino)-5-dimethylaminobenzoic acid (HC Blue No. 13), 1-amino-4-[(2-hydroxyethyl)amino]-2-nitrobenzene (HC Red No. 7), 2-amino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)-amino]-4,6-dinitrophenol, 4-ethylamino-3-nitrobenzoic acid, 2-[(4-amino-2-nitrophenyl)amino]benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,3-benzoxazine (HC Red No. 14), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-uridoethyl)amino]-4-nitrobenzene, 4-[(2,3-dihydroxypropyl)amino]-3-nitro-1-trifluoromethylbenzene (HC Yellow No. 6), 1-chloro-2,4-bis[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 1,4-di[(2,3-dihydroxypropyl)amino]-9,10-anthraquinone, 1-[(2-hydroxyethyl)amino]-4-methylamino-9,10-anthraquinone (CI61505, Disperse Blue No. 3), 2-[(2-aminoethyl)amino]-9,10-anthraquinone (HC Orange No. 5), 1-hydroxy-4-[(4-methyl-2-sulfophenyl)amino]-9,10-anthraquinone, 1-[(3-aminopropyl)amino]-4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (CI62015, Disperse Red No. 11, Solvent Violet No. 26), 1,4-dihydroxy-5,8-bis[(2-hydroxyethyl)amino]-9,10-anthraquinone (CI62500, Disperse Blue No. 7, Solvent Blue No. 69), 9-(dimethylamino)benzo[a]phenoxazin-7-ium chloride (CI51175; Basic Blue No. 6), di[4-(diethylamino)phenyl][4-(ethylamino)naphthyl]carbenium chloride (CI42595; Basic Blue No. 7), 3,7-di(dimethylamino)phenothiazin-5-ium chloride (CI52015; Basic Blue No. 9), di[4-(dimethylamino)phenyl][4-(phenylamino)naphthyl]carbenium chloride (CI44045; Basic Blue No. 26), 2-[(4-(ethyl(2-hydroxyethyl)amino)phenyl)azo]-6-methoxy-3-methylbenzothiazolium methyl sulfate (CI11154; Basic Blue No. 41), 8-amino-2-bromo-5-hydroxy-4-imino-6-[(3-(trimethylammonio)phenyl)amino]-1(4H)-naphthalinone chloride (CI56059; Basic Blue No. 99), bis[4-(dimethylamino)phenyl][4-(methylamino)phenyl]carbenium chloride (CI42535; Basic Violet No. 1), tris[4-(dimethylamino)phenyl]carbenium chloride (CI42555; Basic Violet No. 3), 2-[3,6-(dimethylamino)dibenzopyranium-9-yl]benzoyl chloride (CI45170; Basic Violet No. 10), di(4-aminophenyl)(4-amino-3-methylphenyl)carbenium chloride (CI42510; Basic Violet No. 14), 1,3-bis[(2,4-diamino-5-methylphenyl)azo]-3-methylbenzene (CI21010; Basic Brown No. 4), 1-[(4-aminophenyl)azo]-7-(trimethylammonio)-2-naphthol chloride (CI12250; Basic Brown No. 16), 1-[(4-amino-2-nitrophenyl)azo]-7-(trimethylammonio)-2-naphthol chloride (Basic Brown No. 17), 1-[(4-amino-3-nitrophenyl)azo]-7-(trimethylammonio)-2-naphthol chloride (CI12251; Basic Brown No. 17), 3,7-diamino-2,8-dimethyl-5-phenylphenazinium chloride (CI50240; Basic Red No. 2), 1,4-dimethyl-5-[(4-(dimethylamino)phenyl)azo]-1,2,4-triazolium chloride (CI11055: Basic Red No. 22), 2-hydroxy-1-[(2-methoxyphenyl)azo]-7-(trimethylammonio)naphthalene chloride (CI12245; Basic Red No. 76), 2-[2-((2,4-dimethoxyphenyl) amino)ethenyl]-1,3,3-trimethyl-3H-indol-1-ium chloride (CI48055; Basic Yellow No. 11), 3-methyl-1-phenyl-4-[(3-(trimethylammonio)phenyl)azo]-pyrazol-5-one chloride (CI12719; Basic Yellow No. 57), bis[4-(diethylamino)phenyl]phenylcarbenium hydrogensulfate (1:1) (CI42040; Basic Green No. 1), 1-[di(2-hydroxyethyl)amino]-3-methyl-4-[(4-nitrophenyl)azo]-benzene (CI11210, Disperse Red No 17), 4-[(4-aminophenyl)azo]-1-[di(2-hydroxyethyl)amino]-3-methylbenzene (HC Yellow No. 7), 2,6-dimaino-3-[(pyridin-3-yl)azo]pyridine, 6-hydroxy-5-[(4-sulfophenyl)azo]-2-naphthalenesulfonic acid disodium salt (CI15985; Food Yellow No. 3; FD&C Yellow No. 6) 2,4-dinitro-1-napthol-7-sulfonic acid disodium salt (CI10316; Acid Yellow No. 1; Food Yellow No. 1), 2-(indane-1,3-dion-2-yl)quinoline-x,x-sulfonic acid (mixture of mono- and disulfonic acid) (CI47005: D&C Yellow No. 10; Food Yellow No. 13; Acid Yellow No. 3), 5-hydroxy-1-(4-sulfophenyl)-4-[(4-sulfophenyl)azo]pyrazole-3-carboxylic acid trisodium salt (CI19140; Food Yellow No. 4; Acid Yellow No. 23), 9-(2-carboxyphenyl)-6-hydroxy-3H-xanthen-3-one (CI45350; Acid Yellow No. 73; D&C Yellow No. 8), 5-[(2,4-dinitrophenyl)amino]-2-phenylaminobenzene sulfonic acid sodium salt (CI10385; Acid Orange No. 3), 4-[(2,4-dihydroxyphenyl)azo]benzenesulfonic acid monosodium salt (CI14270; Acid Orange No. 6), 4-[(2-hydroxynapth-1-yl)azo]-benzenesulfonic acid sodium salt (CI15510; Acid Orange No. 7), 4-[(2,4-dihydroxy-3-[(2,4-dimethylphenyl)azo]phenyl)azo]benzenesulfonic acid sodium salt (CI20170; Acid Orange No. 24), 4-hydroxy-3-[(4-sulfonaphth-1-yl)azo]-1-naphthalenesulfonic acid disodium salt (CI14720; Acid Red No. 14), 6-hydroxy-5-[(4-sulfonapth-1-yl)azo]-2,4-naphthalenedisulfonic acid trisodium salt (CI16255; Ponceau 4R; Acid Red No. 18), 3-hydroxy-4-[(4-sulfonaphth-1-yl)azo]-2,7-naphthalenedisulfonic acid trisodium salt (CI16185; Acid Red No. 27), 8-amino-1-hydroxy-2-(phenylazo)-3,6-naphthalenedisulfonic acid disodium salt (CI17200; Acid Red No. 33), 5-(acetylamino)-4-hydroxy-3-[(2-methylphenyl)azo]-2,7-napthalenedisulfonic acid disodium salt (CI18065; Acid Red No. 35), 2-(3-hydroxy-2,4,5,7-tetraiodo dibenzopyran-6-on-9-yl)benzoic acid disodium salt (CI45430; Acid Red No. 51), N-[6-(diethylamino)-9-(2,4-disulfophenyl)-3H-xanthen-3-ylidene]-N-ethylethaneammonium hydroxide, internal salt, sodium salt (CI45100: Acid Red No. 52), 8-[(4-(phenylazo) phenyl)azo]-7-naphthol-1,3-disulfonic acid disodium salt (CI27290; Acid Red No. 73), 2',4',5',7'-tetrabromo-3',6'-dihydroxyspiro[isobenzofuran-1(3H), 9'-[9H]-xanthen]-3-one disodium salt (CI45380; Acid Red No. 87), 2',4',5',7'-tetrabromo-4,5,6,7-tetrachloro-3',6'-dihydroxyspiro[isobenzofuran-1(3H), 9'[9H]xanthen]-3-one disodium salt (CI45410; Acid Red No 92), 3',6'-dihydroxy-4',5'-diiodospiro[isobenzofuran-1(3H), 9'(9H)-xanthen]-3-one disodium salt (CI45425; Acid Red No. 95), (2-sulfophenyl)di[4-(ethyl((4-sulfophenyl)methyl)amino)phenyl]carbenium disodium salt, betaine (CI42090; Acid Blue No. 9; FD&C Blue No. 1), 1,4-bis[(2-sulfo-4-methylphenyl)amino]-9,10-anthraquinone disodium salt (CI61570; Acid Green No. 25), bis[4-(dimethylamino)phenyl](3,7-disulfo-2-hydroxynaphth-1-yl)carbenium internal salt, monosodium salt (CI44090; Food Green No. 4; Acid Green No. 50), bis[4-(diethylamino)phenyl](2,4-disulfophenyl)carbenium internal salt, sodium salt (2:1) (CI42045; Food Blue No. 3; Acid Blue No. 1), bis[4-(diethylamino)phenyl](5-hydroxy-2,4-disulfophenyl)carbenium internal salt, calcium salt (2:1) (CI42051; Acid Blue No. 3) 1-amino-4-(cyclohexylamino)-9,10-anthraquinone-2-sulfonic acid sodium salt (CI62045; Acid Blue No. 62), 2-(1,3-dihydro-3-oxo-5-sulfo-2H-indol-2-ylidene)-2,3-dihydro-3-oxo-1H-indole-5-sulfonic acid disodium salt (CI73015; Acid Blue No. 74), 9-(2-carboxyphenyl)-3-[(2-methylphenyl)amino]-6-[(2-methyl-4-sulfophenyl)amino]-xanthylium internal salt, monosodium salt (CI45190; Acid Violet No. 9), 1-hydroxy-4-[(4-methyl-2-sulfophenyl)amino]-9,10-anthraquinone sodium salt (CI60730; D&C Violet No. 2; Acid Violet No. 43), bis[3-nitro-4-[(4-phenylamino)-3-sulfophenylamino]phenyl]-sulfone (CI10410; Acid Brown No. 13), 5-amino-4-hydroxy-6-[(4-nitrophenyl)azo]-3-(phenylazo)-2,7-naphthalenedisulfonic acid disodium salt (CI20470; Acid Black No. 1), 3-hydroxy-4-[(2-hydroxynaphth-1-yl)azo]-7-nitro-1-naphthalenesulfonic acid chromium complex (3:2) (CI15711; Acid Black No. 52), 3-[(2,4-dimethyl-5-sulfophenyl)azo]-4-hydroxy-1-naphthalenesulfonic acid disodium salt (CI14700; Food Red No. 1; FD&C Red No. 4), 4-(acetylamino)-5-hydroxy-6-[(7-sulfo-4-[(4-sulfophenyl)azo]naphth-1-yl)azo]-1,7-naphthalenedisulfonic acid tetrasodium salt (CI28440; Food Black No. 1) and 3-hydroxy-4-(3-methyl-5-oxo-1-phenyl-4,5-dihydro-1H-pyrazol-4-ylazo)naphthalene-1-sulfonic acid sodium salt, chromium complex (Acid Red No. 195), 3',3",4,5,5',5",6,7-octabromophenolsulfonaphthalein (tetrabromophenol blue), 1-((4-amino-3,5-dimethylphenyl)(2,6-dichlorophenyl)methylene)-3,5-dimethyl-4-imino-2,5-cyclohexadiene joined to phosphoric acid (1:1) (Basic Blue 77), 2',4',5',7'-tetrabromo-4,5,6,7-tetrachloro-3',6'-dihydroxyspiro(isobenzofuran-1(3H), 9'[9H]xanthen]-3-one disodium salt (Acid Red 92), N,N-di(2-hydroxyethyl)-3-methyl-4-((4-nitrophenyl)azo)aniline (Disperse Red 17), 2,4-dinitro-1-naphthol-7-sulfonic acid disodium salt (Acid Yellow 1), 4-((2-hydroxynaphthalene-1-yl)azo)benzosulfonic acid sodium salt (Acid Orange 7), 2-((4-(ethyl(2-hydroxyethyl)amino)-2-methylphenyl)azo)-5-nitro-1,3-thiazole (Disperse Blue 106), 2,4-dinitro-1-naphthol, 2-[(4-aminophenyl)azo]-1,3-dimethyl-1H-imidazo-3-lium chloride, 1-methyl-4-((methylphenylhydrazono)methyl)pyridinium methosulfate, 2-[[4-(dimethylamino)phenyl]-azo]-1,3-dimethylimidazolium chloride, 2-((4-((4-methoxyphenyl)amino)phenyl)azo)-1,3-dimethyl-1H-imidazol-3-ium chloride and 1,3-dimethyl-2-((4-((phenylmethyl)amino)phenyl)azo)-1H-imidazol-3-ium chloride, alone or in combination with one another.

Among the abovementioned direct dyes, particular preference is given to the following compounds—alone or in combination with one another: hydroxyethyl-2-nitro-p-toluidine, 2-hydroxyethylpicramic acid, 4-nitrophenylaminourea, tri(4-amino-3-methylphenyl)carbenium chloride (Basic Violet 2), 1,4-diamino-9,10-anthracenedione (Disperse Violet 1), 1-(2-hydroxyethyl)amino-2-nitro-4-[di(2-hydroxyethyl)amino]benzene (HC Blue No. 2), 4-[ethyl(2-hydroxyethyl)amino]-1-[(2-hydroxyethyl)amino]-2-nitrobenzene hydrochloride (HC Blue No. 12), 1-amino-4-[di(2-hydroxyethyl)amino]-2-nitrobenzene hydrochloride (HC Red No. 13), 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-chloro-6-ethylamino-4-nitrophenol, 2-amino-6-chloro-4-nitrophenol, 4-[(2-hydroxyethyl)amino]-3-nitro-1-trifluoromethylbenzene (HC Yellow No 13), 8-amino-2-bromo-5-hydroxy-4-imino-6-[(3-(trimethylammonio)phenyl)amino]-1(4H)-naphthalinone chloride (CI56059; Basic Blue No. 99), 1-[(4-aminophenyl)azo]-7-(trimethylammonio)-2-naphthyl chloride (CI12250; Basic Brown No. 16), 1-[(4-amino-2-nitrophenyl)azo]-7-(timethylammonio)-2-naphthol chloride (Basic Brown No. 17), 2-hydroxy-1-[(2-methoxyphenyl)azo]-7-(trimethylammonio)naphthalene chloride (CI12245; Basic Red No. 76), 3-methyl-1-phenyl-4-[(3-(trimethylammonio)phenyl)azo]pyrazol-5-one chloride (CI12719; Basic Yellow No. 57) and 2,6-diamino-3-[(pyridin-3-yl)azo]pyridine and salts thereof.

The total amount of the direct dyes in the composition (B) according to the invention is about 0.1 to 90 percent by weight, preferably 1 to 70 percent by weight.

Further dyes that are customary and known for use in hair colorants are described, inter alia, in E. Sagarin, "Cosmetics, Science and Technology", Interscience Publishers Inc., New York (1957), pages 503 ff, and H. Janistyn, "Handbuch der Kosmetika und Riechstoffe" [Handbook of Cosmetics and Fragrances], volume 3 (1973), pages 388 ff. and K. Schrader "Grundlagen und Rezepturen der Kosmetika" [Fundamentals and Formulations of Cosmetics], 2nd edition (1989), pages 782-815, to which reference is hereby expressly made.

The preparation form of the dye carrier mass (A) according to the invention can, for example, be a solution, in particular an aqueous or aqueous-alcoholic solution. However, the particularly preferred preparation forms are a cream, a gel, or an emulsion.

Customary additives in solutions, creams, emulsions or gels are, for example, solvents such as water, lower aliphatic alcohols, for example ethanol, propanol or isopropanol, glycerol or glycols, such as 1,2-propylene glycol, also wetting agents or emulsifiers from the classes of anionic, cationic, amphoteric or nonionogenic surface-active substances, such as, for example, fatty alcohol sulfates, oxyethylated fatty alcohol sulfates, alkylsulfonates, alkylbenzenesulfonates, alkyltrimethylammonium salts, alkylbetaines, oxyethylated fatty alcohols, oxyethylated nonylphenols, fatty acid alkanolamides and oxyethylated fatty acid esters, also thickeners such as higher fatty alcohols, starch, cellulose derivatives, petrolatum, paraffin oil and fatty acids, and also care substances, such as cationic resins, lanolin derivatives, cholesterol, pantothenic acid and betaine. The constituents mentioned are used in the amounts customary for such purposes, for example the wetting agents and emulsifiers in concentrations of from about 0.5 to 30 percent by weight, the thickeners in an amount of from about 0.1 to 30 percent by weight and the care substances in a concentration of from about 0.1 to 5 percent by weight.

Depending on the composition, the color carrier mass (A) can have a weakly acidic, neutral or alkaline reaction. In particular, it has a pH of from 6.5 to 11.5. Basic adjustment takes place here preferably using ammonia, although organic amines, for example monoethanolamine or triethanolamine, or inorganic bases, for example sodium hydroxide or potassium hydroxide, can also be used. For pH adjustment in the acidic range, inorganic or organic acids, for example phosphoric acid, acetic acid, citric acid or tartaric acid, are suitable.

In the color carrier mass (A), antioxidants, such as, for example, ascorbic acid, thioglycolic acid or sodium sulfite, and also complexing agents for heavy metals, for example ethylenediaminotetraacetate or nitriloacetic acid, for example, may also be present in an amount of up to about 0.5 percent by weight. Perfume oils may be present in the color carrier mass according to the invention in an amount of up to about 1 percent by weight. In addition, the component (A) according to the invention can comprise auxiliaries and additives customary for such agents, such as, for example, thickeners, for example homopolymers of acrylic acid, plant gums, algae polysaccharides, amphiphilic associative thickeners, also preservatives; complexing agents; wetting agents or emulsifiers from the classes of anionic, cationic, amphoteric or nonionogenic surface-active substances; alkylating agents (e.g. ammonium salts and/or amino acids, such as, for example, glycine and alanine); and care substances, such as cationic polymers or resins, lanolin derivatives, cholesterol, vitamins, panthothenic acid and betaine. The constituents mentioned are used in the amounts customary for such purposes, for example the wetting agents and emulsifiers in concentrations of from 0.1 to 30 percent by weight and the care substances in a concentration of from 0.1 to 5.0 percent by weight.

The component (C) according to the invention comprises one or more known chemical oxidizing agents, for example hydrogen peroxide or salts or adducts thereof, and persulfates, such as sodium persulfate, potassium persulfate or ammonium persulfate.

Particularly preferred granular compositions of component (B) are dye-containing pellets which are obtained (a) through homogeneous mixing of a starting material comprising at least one natural and/or synthetic dye with a suitable carrier material, and subsequent coating with a suitable encapsulation material, or (b) through coating a suitable carrier material with a mixture of at least one natural and/or synthetic dye and at least one suitable encapsulation material.

Figure 2:
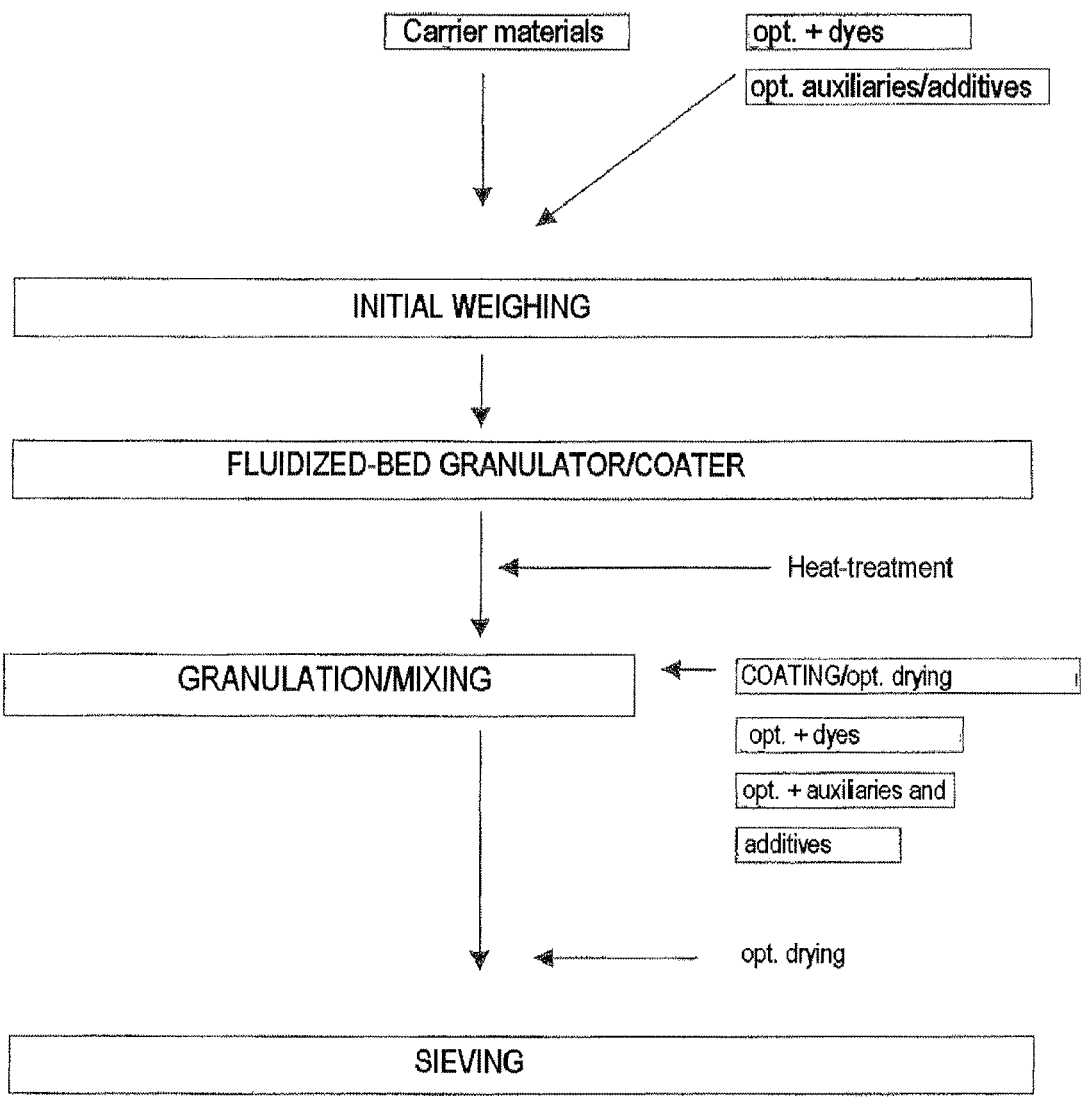
FIG. 2 is a flow chart illustrating a method of producing dye pellets by means of a top spray method.

These dye-containing pellets are produced either by the method shown diagrammatically in FIG. 1 by means of extruder technology [pellets as in (a)] or by the top spray method shown diagrammatically in FIG. 2 [pellets according to (a) or (b)].

For example, the method can be carried out as follows for a 1 kilogram batch, it being necessary to adapt the spray air pressure and the spray rate appropriately for larger batches:

1. Production by Means of Extruder Technology:

For this, in a vertical granulator (rotor speed=50 to 200 rpm, preferably about 150 rpm; chopper speed=750 to 1250 rpm, preferably about 1000 rpm) at room temperature (15 to 35° C.), a base mass is produced by dry-mixing and subsequent wet-mixing of the dye mass with the carrier materials and optionally antioxidants and further auxiliaries. This base mass is then extruded in an extruder (speed=15 to 50 rpm, preferably about 25 to 30 rpm; perforation size of the screen=about 0.01 to 5 mm; preferably 0.1 to 3 mm and in particular 0.6 to 1 mm) and the granules obtained in this way are rounded in a pelletizer (speed=400 to 800 rpm; preferably about 500 to 600 rpm). The granules are then dried at a product temperature of from 20 to 60° C. (preferably 30 to 55° C.) (inlet air temperature preferably about 70 to 80° C.) and subsequently (if appropriate after prior heating to 40-50° C.) coated using a fluidized-bed method (spray rate preferably about 5 to 20 g/min; spray air pressure preferably about 1.5 to 2.5 bar), where the amount of encapsulation material used (based on the amount of granules to be coated) is 0.5 to 50 percent by weight, preferably 1 to 20 percent by weight and in particular 2 to 15 percent by weight. Finally, the product is dried (product temperature max. about 60° C.).

2. Production by Means of Top Spray Method:
(a) For this, in a fluidized-bed granulator/coater at room temperature (15 to 35° C.), the dye mass is mixed with the carrier materials and optionally antioxidants and further auxiliaries. The base mass obtained in this way is then heat-treated (product temperature max. about 55° C.), then granulated (spray rate preferably about 6 to 20 g/min; spray air pressure preferably about 0.25 to 2.5 bar), where the amount of encapsulation material used (based on the amount of granules to be coated) is 0.5 to 50 percent by weight, preferably 1 to 20 percent by weight and in particular 2 to 10 percent by weight; and then optionally coated. If required, the product is finally dried (product temperature max. about 60° C.).
(b) For this, in a fluidized-bed granulator/coater at room temperature (15 to 35° C.) the carrier materials and optionally antioxidants and further auxiliaries are mixed together. The base mass obtained in this way is then heat-treated (product temperature max. about 55° C.), then granulated and then coated with a solution/dispersion of the dyes and optionally antioxidants and further auxiliaries in a suitable encapsulation material (spray rate preferably about 6 to 20 g/min; spray air pressure preferably about 0.25 to 2.5 bar), where the amount of encapsulation material used (based on the amount of granules to be coated) is 0.5 to 50 percent by weight, preferably 1 to 20 percent by weight and in particular 2 to 10 percent by weight. If required, the product is finally dried (product temperature max. about 60° C.).

Suitable carrier materials for the dye-containing pellets are pulverulent, microcrystalline substances which convert the dyes to a physical state which makes it possible to carry out the method for coating the pellets with suitable encapsulation materials.

Suitable carrier materials are, in particular, gum arabic, dextrose, polyvinylpyrrolidone, oligosaccharides, microcrystalline cellulose derivatives, such as, for example, hydroxypropylmethylcellulose, methylcellulose, hydroxyethylcellulose, hydroxypropylcellulose, nonoxynolhydroxyethylcellulose and cetylhydroxyethylcellulose or physically or chemically modified starches or starch derivatives, such as, for example, starch esters (for example acetylated starches), starch ethers (for example hydroxyalkylated starches), dialdehyde starches, dicarboxyl starches, distarch phosphates, hydroxyalkyl starch phosphates or hydroxyalkyl starches, where the alkyl groups preferably comprise 1 to 4, particularly preferably 2 to 3, carbon atoms. Also suitable are crosslinked starch ethers, such as, for example, those with the INCI names Dimethylimidazolidone Rice or Corn Starch or hydrophobically modified starches (for example those with the INCI name Aluminium Starch Octensuccinate). The starch may have been modified either thermally or hydrolytically or enzymatically, it being possible to obtain the starting starch from the known sources, for example corn, potatoes, sweet potatoes, peas, bananas, oats, wheat, barley, rice, sago, tapioca, arrowroot, amaranth, canna, sorghum, etc. Particularly preferred starch derivatives are nonionic starch derivatives, in particular nonionic starch derivatives modified with alkylene oxides such as ethylene oxide, propylene oxide or butylene oxide, acetanhydride or butyl ketene dimer, and in particular propylene oxide. Further suitable carrier materials are synthetic calcium silicate, kieselguhr, silicon dioxide or other non-caking powders.

Suitable encapsulation materials for the pellets according to the invention are water-soluble or waterdispersible, film-forming substances which are able to deposit, from solutions or dispersions, uniform films on the pellets by spray-drying in such a way that it can be thought of as coating.

Suitable encapsulation materials are gum arabic, cellulose derivatives (for example methylcelluloses), polyethylene dispersions, polyacrylic acids, polyvinyl alcohols, polycarbonates, polyvinylpyrrolidone, polyesters and polyamides or natural film formers, such as, for example, chitosan, shellac, oligosaccharides and also Chinese balsam resin (colophony).

The pellets used preferably have a particle diameter of from 100 μm to 1000 μm, in particular a particle diameter of from 120 μm to 1500 μm.

For the application, directly prior to use, components (A) and (B) and in the case of oxidative coloration or the simultaneous lightening and coloring of hair, additionally component (C) are mixed together, and an amount of the thus prepared individually tailored colorant sufficient for the hair-dyeing treatment, generally about 60 to 200 grams, depending on the fullness of the hair, is applied to the hair.

If lightening is desired, suitable keratin-lightening substances (in particular persulfates and mixtures of persulfates and hydrogen peroxide) may be present in component (B).

The agent (C) according to the invention can comprise at least one source of an oxidizing agent. Preferred oxidizing agents are water-soluble peroxide-containing oxidizing agents. "Water-soluble" means here that, under standard conditions, at least 0.1 g, preferably 1 g and in particular 10 g, of the oxidizing agent can be dissolved in 1 liter of demineralized water. The oxidizing agents are useful for the initial solubilization and decoloring of the melanin (bleaching) and the oxidation of the oxidation dye precursors (oxidative coloring) in the hair shaft.

Any known water-soluble oxidizing agent can be used within the scope of the present invention, preference being given to inorganic peroxides which form hydrogen peroxide in an aqueous solution. Water-soluble peroxide-containing oxidizing agents are sufficiently known from the prior art and include hydrogen peroxide, inorganic metal peroxides, such as, for example, sodium periodate or sodium peroxide, organic peroxides, such as, for example, urea peroxide or melamine peroxide and inorganic persalt bleaches, such as, for example, alkali metal salts of the perborates, percarbonates, perphosphates, persilicates, persulfates and the like. These inorganic persalts may also be present as monohydrates, tetrahydrates, etc. Alkyl and aryl peroxides and/or peroxidases may likewise be used. If desired, mixtures of 2 or more of these oxidizing agents can also be used. The oxidizing agents may be in the form of an aqueous solution or a powder which is dissolved prior to use. Preferred oxidizing agents according to the present invention are hydrogen peroxide, percarbonates, persulfates and combinations of these compounds.

According to the present invention, the agents comprise about 0.1 to about 15 percent by weight, preferably about 1 to 10 percent by weight, and in particular about 2 to about 7 percent by weight, of the oxidizing agent. A further preferred oxidizing agent is a source of peroxymonocarbonate ions, which is preferably formed in situ from a hydrogen peroxide source and a hydrogen carbonate source. Oxidizing agents of this type are particularly effective at a pH of less than or equal to 9.5, with a pH of from 7.5 to 9.5 and in particular about 9 being preferred. In addition, this system is particularly effective in combination with a source for ammonia or ammonium ions. It has been found that oxidizing agents can have a positive effect on the desired hair-dyeing results coupled with a significant reduction in odor, skin and scalp irritations and hair damage.

Any source of these ions can be used, with suitable sources which may be mentioned being, for example, sodium, potassium, guanidine, arginine, lithium, calcium, magnesium, barium or ammonium salts of the carbonates, carbamates and hydrogencarbonates, and mixtures thereof, for example sodium carbonate, sodium hydrogencarbonate, potassium carbonate, potassium hydrogencarbonate, guanidine carbonate, guanidine hydrogencarbonate, lithium carbonate, calcium carbonate, magnesium carbonate, barium carbonate, ammonium carbonate, ammonium hydrogencarbonate and mixtures thereof. Percarbonate salts can simultaneously serve as a source of carbonate ions and as oxidizing agent. Preferred sources of carbonates, carbamates and hydrogencarbonates are sodium hydrogencarbonate, potassium hydrogencarbonate and ammonium carbamate, and mixtures thereof.

According to the present invention, the agents comprise about 0.1 to about 15 percent by weight, preferably about 1 to about 10 percent by weight and in particular about 1 to about 8 percent by weight, of a hydrogencarbonate ion and about 0.1 to 10 percent by weight, preferably about 1 to 7 percent by weight and in particular about 2 to about 6 percent by weight, of a hydrogen peroxide source.

According to the present invention, the agents can optionally also comprise at least one source of an alkalinizing agent, preferably a source of ammonia or ammonium ions. An alkalinizing agent which may be used is any known compound, for example alkanolamides such as, for example, monoethanolamine, diethanolamine, triethanolamine, monopropanolamine, dipropanolamaine, tripropanolamine, 2-amino-2-methyl-1,3-propanediol, 2-amino-2-methyl-1-propanol or 2-amino-2-hydroxymethyl-1,3-propanediol, and guanidium salts. Particularly preferred alkalinizing agents are those agents which have a source of ammonium ions, where any source of ammonium ions is suitable. Preferred sources of ammonium ions are ammonium chloride, ammonium sulfate, ammonium nitrate, ammonium phosphate, ammonium acetate, ammonium carbonate, ammonium hydrogencarbonate, ammonium carbamate, ammonium hydroxide, percarbonate salts, ammonia and mixtures thereof. Particular preference is given here to ammonium carbonate, ammonium carbamate, ammonium hydrogencarbonate, ammonia and mixtures thereof. The agents according to the present invention can comprise about 0.1 to about 10 percent by weight, preferably about 0.5 to about 5 percent by weight, and in particular about 1 to about 3 percent by weight, of an alkalinizing agent, preferably ammonium ions.

According to the present invention, the agents may also comprise a source of a free-radical scavenger. In the present case, the term "free-radical scavenger" describes a compound which reacts with a reactive free radical, preferably carbonate free radicals, in order to convert these reactive free radicals into a less reactive compound by means of a series of rapid reactions.

Suitable free-radical scavengers are compounds of the general formula (I)

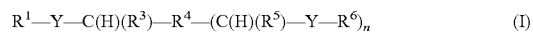

$$R^1-Y-C(H)(R^3)-R^4-(C(H)(R^5)-Y-R^6)_n \qquad (I)$$

where Y is $NR^2$, O, or S, preferably $NR^2$, n is 0 to 2, and in which $R^4$ is a monovalent or divalent radical from the group consisting of: (a) substituted or unsubstituted, straight-chain or branched alkyl or mono- or polyunsaturated alkyl or heteroalkyl groups and aliphatic, heteroaliphatic or heteroolefinic systems, (b) substituted or unsubstituted, mono- or polycyclic aliphatic, aromatic or heterocyclic systems, or (c) substituted or unsubstituted, mono-, poly- or perfluorinated alkyl systems; where the systems (a), (b) and (c) have 1 to 12 carbon atoms and 0 to 5 heteroatoms (O, S, N, P, Si); and in which $R^4$, together with $R^3$ or $R^5$, form a 5-, 6- or 7-membered ring; and in which $R^1$, $R^2$, $R^3$, $R^5$ and $R^6$ are monovalent and, independently of one another, are one of the above described groups (a), (b) or (c) or hydrogen.

$R^4$ is preferably (a) a substituted or unsubstituted, straight-chain or branched alkyl or heteroalkyl group, or an aliphatic, heteroaliphatic or heteroolefinic system, (b) a substituted or unsubstituted, mono- or polycyclic aliphatic, aromatic or heterocyclic system, or (c) a substituted or unsubstituted, mono-, poly- or perfluorinated alkyl system, where $R^4$ is particularly preferably a substituted or unsubstituted, straight-chain or branched alkyl or heteroalkyl group, or an aliphatic or heteroaliphatic system (b) a substituted or unsubstituted aromatic or heterocyclic system, (c) a substituted or unsubstituted, mono-, poly- or perfluorinated alkyl system and in particular a substituted or unsubstituted, straight-chain or branched alkyl or heteroalkyl group. Preferably, the above described $R^4$ groups (a), (b), and (c) have 1 to 8 carbon atoms, where 1 to 6 carbon atoms and in particular 1 to 4 carbon atoms are particularly preferred, and 0 to 3 heteroatoms, preferably 0 to 2 heteroatoms and in particular 1 heteroatom. If the system has heteroatoms, it preferably comprises 1 heteroatom. The heteroatom to be mentioned is, in particular: O, S and N, where O and N, in particular O, are preferred. $R^1$, $R^2$, $R^3$, $R^4$, $R^5$ and $R^6$ independently of one another, are hydrogen or one of the systems specified for $R^4$.

Alternatively, $R^1$, $R^2$, $R^3$, $R^4$, $R^5$, and $R^6$ may also be substituted; where the substituent is preferably chosen from: (a) C-linked monovalent substituents from the group of (i) substituted or unsubstituted, straight-chain or branched alkyl radicals, mono- or polyunsaturated alkyl, heteroalkyl, aliphatic, heteroaliphatic or heteroolefinic systems, (ii) substituted or unsubstituted, mono- or polycyclic aliphatic, aromatic or heterocyclic systems, or (iii) substituted or unsubstituted, mono-, poly- or perfluoroalkyl systems; where the abovementioned systems (i), (ii) and (iii) comprise 1 to 10 carbon atoms and 0 to 5 heteroatoms (O, S, N, P, Si); (b) S-linked monovalent substituents from the group $SA^1$, SCN, $SO_2A^1$, $SO_3A^1$, $SSA^1$, $SOA^1$, $SO_2NA^1A^2$, $SNA^1A^2$ and $SONA^1A^2$; (c) O-linked monovalent substituents from the group $OA^1$, OCN and $ONA^1A^2$; (d) N-linked monovalent substituents from the group $NA^1A^2$, $(NA^1A^2A^3)^+$, NC, $NA^1OA^2$, $NA^1SA^2$, NCO, NCS, $NO_2$, $N\!\!=\!\!NA^1$, $N\!\!=\!\!NOA^1$, $NA^1CN$, $NA^1NA^2A^3$; (e) the monovalent substituents $COOA^1$, $CON_3$, $CONA^1{}_2$, $CONA^1COA^2$, $C(\!\!=\!\!NA^1)NA^1A^2$, CHO, CHS, CN, NC and X; and (f) fluoroalkyl monovalent substituents from the group mono-, poly-, or perfluoroalkyl systems having 1 to 12 carbon atoms and 0 to 4 heteroatoms.

In the abovementioned groups (b) to (e), $A^1$, $A^2$ and $A^3$ are monovalent and, independently of one another, are (1) H, (2) substituted or unsubstituted, straight-chain or branched alkyl groups, mono- or polyunsaturated alkyl groups, heteroalkyl groups, aliphatic, heteroaliphatic or heteroolefinic systems, (3) substituted or unsubstituted, mono- or polycyclic aliphatic, aromatic or heterocyclic systems, or (4) substituted or unsubstituted mono-, poly- or perfluoroalkyl systems; where the above-mentioned systems (2), (3) and (4) have 1 to 10 carbon atoms and 0 to 5 heteroatoms (O, S, N, P, Si); and in which X is a halogen atom (F, Cl, Br, I).

Preferred substituents have a Hammett sigma para ($\sigma_p$) value of from −0.65 to +0.75, preferably −0.4 to +0.5. Hammett sigma values are described in the literature "Advanced Organic Chemistry—Reactions, Mechanisms and Structure" (Jerry March, 5th ed. (2001) at pages 368-375), to which reference is hereby expressly made.

Likewise suitable free-radical scavengers are compounds of the general formula (II):

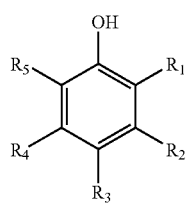

(II)

where $R_1$, $R_2$, $R_3$, $R_4$ and $R_5$, independently of one another, are H, $COO^-M^+$, Cl, Br, $SO_3^-M^+$, $NO_2$, $OCH_3$, OH or a $C^1$ to $C^{10}$ primary or secondary alkyl group and M is either H or an alkali metal atom. Preferably, the abovementioned free-radical scavengers have a pKa value of 8.5 in order to ensure protonation of the hydroxy group. Further suitable free-radical scavengers are those which are chosen from the group (III) consisting of benzylamine, imidazole, di-tert-butylhydroxytoluene, hydroquinone, guanine, pyrazine, piperidine, morpholine, methylmorpholine, 2-methoxyethylamine and mixtures thereof. Free-radical scavengers preferred according to the present invention are alkanolamines, amino sugars, amino acids, amino acid esters and mixtures thereof. Particular preference is given to: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophane and mixtures thereof, and salts thereof, such as, for example, potassium, sodium and ammonium salts or mixtures thereof. Particularly preferred compounds are glycine, sarcosine, lysine, serine, 2-methoxyethylamine, glucosamine, glutamic acid, morpholine, piperidine, ethylamine, 3-amino-1-propanol and mixtures thereof. The free-radical scavengers according to the present invention preferably have a molecular weight below about 500, preferably less than about 300, in particular less than about 250, in order to facilitate penetration of the free-radical scavenger into the hair fibers. The agents according to the present invention comprise—if they comprise a free-radical scavenger—preferably about 0.1 to about 10 percent by weight, in particular 1 to 7 percent by weight, of the free-radical scavenger. The free-radical scavenger is preferably chosen so that it is not from the same compound type as the alkalinizing agent. According to one embodiment of the present invention, the free-radical scavenger can also be formed in situ prior to use in the hair colorant.

The mixture is then left to act on the hair at 15 to 50 degrees Celsius for 10 to 45 minutes, preferably 15 to 30 minutes, then the hair is rinsed with water and dried. This rinsing may be followed by additionally washing the hair with a shampoo and, if appropriate, after-rinsing it with a weak organic acid, such as, for example, citric acid or tartaric acid. Finally the hair is dried.

Whereas colorants according to the prior art are manufactured industrially and are already nuanced in a ready-to-use form, the dyeing method according to the invention provides the person skilled in the art with any combination, tailored to the color nuance desired in each case, of the color base tones present in powder or granule form (orange, red, blue, yellow, etc.) and if appropriate keratin-lightening compounds. The hairdresser thus no longer has to keep a large number of individual color nuances in stock, but can prepare the desired color nuances with a few components (about 7-10 dye premixes (base tones) in powder or granule form; only a single base mass and additionally a peroxide carrier). Besides reducing the storage expenditure for the colorants and bleaching agents, the method according to the invention also permits a significantly greater nuance diversity and creativity of the person skilled in the art.

The examples below are intended to illustrate the subject matter of the invention in more detail but without limiting it.

EXAMPLES

Example 1

Production of Dye Pellets in the Top Spray Method

In a Glatt fluidized-bed granulator and coater, the following mixture A is heated to a product temperature of 34° C. at an inlet air temperature of 90° C. and an amount of air of 18 m³/h.

| Dye pellet premix | |
|---|---|
| 381.2 g | 4-(2-Hydroxethylamino)-3-nitrophenol |
| 101.0 g | 2-((2-Hydroxyethyl)amino)-4,6-dinitrophenol |
| 100.0 g | Corn starch |

Then, a 20% strength aqueous polyvinylpyrrolidone solution ("spray solution") is sprayed onto this premix with an initial spray rate of 8 g/min and a spray air pressure of 0.5 bar. In the course of the granulation process, the spray rates are increased to 12 g/min and the inlet air temperature to 100° C., the amount of air being increased to a maximum of 30 m³/h. The product temperature is maintained at about 30-31° C. throughout the entire process. After applying 310 g, the pellets are dried at a maximum product temperature of 57° C., then cooled to about 30° C. and sieved.

Example 2

Production of Dye Pellets by Means of Extruder Technology

| Dye pellet premix | |
|---|---|
| 1896 g | 4-(2-Hydroxyethylamino)-3-nitrophenol |
| 504 g | 2-((2-Hydroxyethyl)amino)-4,6-dinitrophenol |
| 800 g | Microcrystalline cellulose |
| 800 g | Corn starch |

The dye pellet premix is mixed in a vertical granulator (rotor speed=about 150 rpm; chopper speed=about 1000 rpm) for 1 minute and then sprayed with 2091 g of a 6% strength aqueous hydroxypropylmethylcellulose solution using a two-component nozzle with further mixing. The resulting mass is extruded using an extruder model BR 200 (speed=27 rpm; sieve Ø: 1.0 mm) at a product temperature of about 30° C. The material obtained in this way is then rounded in a pelletizer model P 50 1 minute at 550 rpm and then dried in a Glatt vertical granulator at an inlet air temperature of 70° C. and with an amount of air of about 60-90 m³/h and a maximum product temperature of 51° C.

In a Glatt fluidized-bed granulator and coater, 1500 g of the dried dye pellet are heated to a product temperature of 39-40° C. at an inlet air temperature of about 50° C. and with an amount of air of 75 m³/h. The pellets are then sprayed with a 10% strength aqueous hydroxypropylmethylcellulose solution at a spray rate of 5 g/min and a spray air pressure of 2.5 bar, the spray rate being increased to 8.5 g/min in the course of the process. After applying 2215 g of the spray solution, corresponding to a 14% strength solids application, the pellets are again dried at a product temperature of at most 51° C. (inlet air temperature=about 70° C.), then cooled to about 27° C. and sieved. [Alternatively, drying and coating or granulation, drying and coating can also be carried out in a common process step.]

Example 3

Production of Dye Pellets by Means of Extruder Technology

| Dye pellet premix | |
|---|---|
| 1411 g | 2,5-Diaminotoluene sulfate |
| 636 g | 4-Amino-2-hydroxytoluene |
| 353 g | 2-Amino-4-(β-hydroxyethylamino)anisole sulfate |
| 794 g | Ascorbic acid |
| 1058 g | Sodium sulfite |
| 800 g | Hydroxypropylcellulose |
| 1300 g | Corn starch |

The preparation takes place analogously to Example 2 although a 5.625% strength aqueous hydroxypropylmethylcellulose solution is used as coating agent.

Example 4

Production of Dye Pellets in the Top Spray Method

| Dye pellet premix | |
|---|---|
| 7.2 g | 5-Amino-2-methylphenol |
| 16.0 g | 2,5-Diaminotoluene sulfate |
| 4.0 g | 2-Amino-4-(β-hydroxyethylamino)anisole sulfate |
| 3.0 g | Ascorbic acid |
| 4.0 g | Sodium sulfite |
| 965.8 g | Hydrolyzed corn starch (oligosaccharide) |

The dye pellet premix is pelletized in the manner described in Example 1 with 563 g of a 20% strength aqueous polyvinylpyrrolidone solution.

Example 5

Production of Dye Pellets in the Top Spray Method

| Dye pellet premix | |
|---|---|
| 38.6 g | 2,4-Diaminophenoxyethanol hydrochloride |
| 47.1 g | N,N-bis(2-hydroxyethyl)-p-phenylenediamine sulfate |
| 3.0 g | HC Blue No. 15 |
| 30.0 g | Ascorbic acid |
| 10.0 g | Ethylenediaminotetraacetic acid disodium salt |
| 500.0 g | Gum arabic, 20% strength solution in water |
| Filling material | |
| 771.3 g | Hydrogenated saccharides (main constituent: 6-O-α-glucopyranolyl-D-sorbitol and 1-O-α-glucopyranolyl-D-mannitol) |

In a Glatt fluidized-bed granulator and coater, the filling material is initially introduced and heated to a product temperature of about 34° C. at an inlet air temperature of 75° C. and an amount of air of 55-65 m³/h. The aqueous dye pellet premix ("spray solution") is then sprayed onto the initially introduced filling material with an initial spray rate of 15-22 g/min and a spray air pressure of 1.2-1.4 bar. In the course of the granulation process, the spray rate and the inlet air temperature are kept constant. The amount of air is increased to a maximum of 100 m³/h depending on the dye pellet premix. The product temperature is kept between 40 and 60° C. throughout the entire process depending on the dye pellet premix. After applying the dye pellet premix, the pellets are dried at a maximum product temperature of 60° C., then left to cool to about 30° C. and sieved.

Example 6

Production of Dye Pellets in the Top Spray Method

| | Dye pellet premix |
|---|---|
| 63.0 g | 1-Hydroxethyl-4,5-diaminopyrazole sulfate |
| 32.5 g | 4-Amino-2-hydroxytoluene |
| 2.0 g | HC Red No. 10/HC Red No. 11 (in the ratio 70:30) |
| 30.0 g | Ascorbic acid |
| 10.0 g | Ethylenediaminotetraacetic acid disodium salt |
| 500.0 g | Gum arabic, 20% strength solution in water Filling material |
| 762.5 g | Hydrogenated saccharides (main constituent: 6-O-α-glucopyranolyl-D-sorbitol and 1-O-α-glucopyranolyl-D-mannitol) |

In a Glatt fluidized-bed granulator and coater, the filling material is initially introduced and heated to a product temperature of about 34° C. at an inlet air temperature of 75° C. and an amount of air of 55-65 m³/h. The aqueous dye pellet premix ("spray solution") is then sprayed onto the initially introduced filling material with an initial spray rate of 15-22 g/min and a spray air pressure of 1.2-1.4 bar. In the course of the granulation process, the spray rate and the inlet air temperature are kept constant. The amount of air is increased to a maximum of 100 m³/h depending on the dye pellet premix. The product temperature is kept between 40 and 60° C. throughout the entire process depending on the dye pellet premix. After applying the dye pellet premix, the pellets are dried at a maximum product temperature of 60° C., then left to cool to about 30° C. and sieved.

Example 7

Production of Dye Pellets in the Top Spray Method

| | Dye pellet premix |
|---|---|
| 12.0 g | 4-Amino-3-methylphenol |
| 12.0 g | 4-Amino-2-hydroxytoluene |
| 80.0 g | 4-Amino-6-chloro-4-nitrophenol |
| 30.0 g | Ascorbic acid |
| 10.0 g | Ethylenediaminotetraacetic acid disodium salt |
| 500.0 g | Gum arabic, 20% strength solution in water Filling material |
| 756.0 g | Hydrogenated saccharides (main constituent: 6-O-α-glucopyranolyl-D-sorbitol and 1-O-α-glucopyranolyl-D-mannitol) |

In a Glatt fluidized-bed granulator and coater, the filling material is initially introduced and heated to a product temperature of about 34° C. at an inlet air temperature of 75° C. and an amount of air of 55-65 m³/h. The aqueous dye pellet premix ("spray solution") is then sprayed onto the initially introduced filling material with an initial spray rate of 15-22 g/min and a spray air pressure of 1.2-1.4 bar. In the course of the granulation process, the spray rate and the inlet air temperature are kept constant. The amount of air is increased to a maximum of 100 m³/h depending on the dye pellet premix. The product temperature is kept between 40 and 60° C. throughout the entire process depending on the dye pellet premix. After applying the dye pellet premix, the pellets are dried at a maximum product temperature of 60° C., then left to cool to about 30° C. and sieved.

Example 8

Cream-like Hair Colorant

| | Cream base (A) |
|---|---|
| 8.70 g | Cetylstearyl alcohol |
| 2.30 g | Glyceryl stearate (self-emulsifying) |
| 0.80 g | Lanolin |
| 3.80 g | Lanolin alcohol |
| 1.42 g | Sodium cetylstearyl sulfate |
| 0.07 g | Formaldehyde |
| 0.01 g | Tocopherol |
| 0.20 g | Perfume |
| 10.00 g | Ammonia |
| ad 100.00 g | Water |

The above cream base (component A) is prepared in a classical hot-emulsification process. Prior to use, 50 g of the above cream base (component A) are mixed with 6 g of dye pellets according to one of Examples 1 or 2 (component B) in a dyeing dish or shaking bottle.

Example 9

Oxidation Hair Colorant

| | Cream base (A) |
|---|---|
| 8.70 g | Cetylstearyl alcohol |
| 2.30 g | Glyceryl stearate (self-emulsifying) |
| 0.80 g | Lanolin |
| 3.80 g | Lanolin alcohol |
| 1.42 g | Sodium cetylstearyl sulfate |
| 0.07 g | Formaldehyde |
| 0.01 g | Tocopherol |
| 0.20 g | Perfume |
| 10.00 g | Ammonia |
| ad 100.00 g | water |
| Oxidizing agent (C) Hydrogen peroxide emulsion | |
| 9.00 g | Hydrogen peroxide |
| 1.80 g | Cetylstearyl alcohol |
| 3.30 g | Polyvinylpyrrolidone/styrene copolymer |
| 0.20 g | Disodium phosphate |
| 0.20 g | Sodium lauryl sulfate |
| 0.10 g | Salicylic acid |
| 0.08 g | Phosphoric acid |
| ad 100.00 g | Water |

The above hydrogen peroxide emulsion is prepared in a classical hot-emulsification process. Directly prior to use, 60 g of this hydrogen peroxide emulsion (component C) are mixed with 60 g of the cream base (component A) and 6 g of dye pellets according to Example 3 or 4 (component B) in a dyeing dish or shaking bottle.

Example 10

Multicomponent Kit for Dyeing Hair

TABLE 1

Dye carrier mass (A) (Amount in %)

|  | Liquid 1 | Liquid 2 | Liquid 3 | Gel 1 | Gel 2 | Gel 3 | Cream 1 | Cream 2 | Cream 3 |
|---|---|---|---|---|---|---|---|---|---|
| Olein | 20 | 10 | 15 | 15 | 10 | 10 | — | 2 | 2 |
| Fatty alcohol alkoxylate | 15 | 10 | 10 | 15 | 10 | 15 | 6 | 6 | — |
| Isopropanol | 15 | 15 | 17 | 15 | 12 | 16 | — | — | 1 |
| Glycol distearate | — | — | — | 4 | — | — | 2 | — | — |
| Fatty alcohols | 5 | 10 | 5 | — | 12 | 12 | 16 | 14 | 18 |
| Lauryl ether sulfate | 10 | 5 | — | 10 | 10 | — | 10 | 5 | — |
| Behentrimonium chloride | — | — | 1 | — | — | 3 | — | — | 5 |
| Polyquats | 1 | 2 | 1 | 1 | 1 | 2 | 1 | 1 | 1 |
| Cocamide MEA | — | — | — | — | — | 3 | — | 6 | 5 |
| Glyceryl laurate | — | — | — | — | — | 3 | — | 4 | — |
| Water | ad 100 | | | | | | | | |

TABLE 2

Dye powder (B) (amount in %)

| Dyes | Color | | | | | | | | |
|---|---|---|---|---|---|---|---|---|---|
|  | Yellow | Gold | Orange | Red | Violet | Pink | Blue | Brown | Grey |
| 2,5-Diamino-p-tolylenediamine sulfate |  |  |  |  |  |  |  |  | 4.95 |
| 2,4-Diaminophenoxyethanol *HCl |  |  |  |  |  |  | 3.86 |  |  |
| p-Phenylenediamine |  |  |  |  |  |  |  | 2.4 |  |
| p-Aminophenol |  |  | 1.5 |  |  |  |  |  |  |
| Resorcinol |  |  |  |  |  |  |  | 1.8 |  |
| m-Aminophenol |  |  |  |  |  |  |  | 0.64 |  |
| 4-Amino-2-hydroxytoluene |  |  | 2.05 | 1.12 | 1.17 |  |  |  |  |
| 1-Naphthol |  |  |  |  |  |  | 1.73 |  |  |
| 6-Amino-m-cresol | 1.5 |  |  |  |  |  |  |  |  |
| Hydroxyethyl-3,4-methylenedioxyaniline *HCl |  |  |  |  |  |  |  |  | 4.9 |
| N,N-bis(2-hydroxyethyl)-p-phenylenediamine*sulfate |  |  |  |  | 2.8 |  |  | 4.71 |  |
| 1-(β-Hydroxyethyl)-4,5-diaminopyrazole*sulfate |  |  |  | 2.18 |  | 2.88 |  |  |  |
| 2-Amino-6-chloro-4-nitrophenol |  | 2.0 |  |  |  |  |  |  |  |
| N-(2-hydroxyethyl)-2-nitro-4-trifluoromethylaniline |  |  |  |  |  |  |  |  | 3.0 |

| Oxidizing agent (C): Hydrogen peroxide emulsion | |
|---|---|
| 9.00 g | Hydrogen peroxide |
| 1.80 g | Cetylstearyl alcohol |
| 3.30 g | Polyvinylpyrrolidone/styrene copolymer |
| 0.20 g | Disodiumphosphate |
| 0.20 g | Sodium lauryl sulfate |
| 0.10 g | salicylic acid |
| 0.08 g | Phosphoric acid |
| ad 100.00 g | Water |

Directly prior to use, 60 g of the abovementioned hydrogen peroxide emulsion (C) are mixed with in each case 6 g of the dye powder (B) according to Table 2 and 60 g of the dye carrier mass (A) as in Table 1 in a dyeing dish or shaking bottle and applied to the hair. After a contact time of 30 minutes at 40° C., the hair is rinsed with lukewarm water, washed with a standard commercial shampoo, rinsed with lukewarm water and then dried. The colors obtained are given in Table 2.

Unless stated otherwise, all of the percentages are percentages by weight.

The invention claimed is:

1. A multicomponent kit for dyeing keratin fibers, said multicomponent kit consisting of:
    a dye carrier mass (A) that is free from dyes and dye precursors;
    a granular composition (B) which comprises at least one oxidation dye precursor and/or at least one direct dye and optionally at least one keratin-lightening or bleaching substance; and optionally
    a suitable oxidizing agent (C) wherein
    the granular composition (B) is a dye-containing pellet which is obtained through homogeneous mixing of a starting material comprising at least one natural and/or synthetic dye with a carrier material and subsequent coating with an encapsulation material.

2. A multicomponent kit for dyeing keratin fibers, said multicomponent kit consisting of:
    a dye carrier mass (A) which is free from dyes and dye precursors;

a granular composition (B) which comprises at least one oxidation dye precursor and/or at least one direct dye and optionally at least one keratin-lightening or bleaching substance; and optionally a suitable oxidizing agent (C) wherein the granular composition (B) is a dye-containing pellet which is obtained through coating a carrier material with a mixture of at least one natural and/or synthetic dye and at least one encapsulation material.

3. A multicomponent kit for dyeing keratin fibers, said multicomponent kit consisting of:

a dye carrier mass (A) which is free from dyes and dye precursors;

a granular composition (B) which comprises at least one oxidation dye precursor and/or at least one direct dye and optionally at least one keratin-lightening or bleaching substance; and optionally a suitable oxidizing agent (C)

wherein the granular composition (B) is a dye-containing pellet which is obtained through homogeneous mixing of a starting material comprising at least one natural and/or synthetic dye with a carrier material and subsequent coating with an encapsulation material and in the case of the dye pellet, the carrier material is chosen from gum arabic, polyvinylpyrrolidones, dextrose, oligosaccharides, microcrystaline cellulose derivatives physically or chemically modified starches or starch derivatives, synthetic calcium silicate, kieselguhr, silicon dioxide or other non-caking powders.

4. A multicomponent kit for dyeing keratin fibers, said multicomponent kit consisting of:

a dye carrier mass (A) which is free from dyes and dye precursors;

a granular composition (B) which comprises at least one oxidation dye precursor and/or at least one direct dye and optionally at least one keratin-lightening or bleaching substance: and optionally a suitable oxidizing agent (C)

wherein the granular composition (B) is a dye-containing pellet which is obtained through homogeneous mixing of a starting material comprising at least one natural and/or synthetic dye with a carrier material and subsequent coating with an encapsulation material and in the case of the dye pellet, the carrier material is chosen from gum arabic, polyvinylpyrrolidone, dextrose, oligosaccharides, hyroxypropylmethylcellulose methylcellulose, hydroxyethylcellulose, hydroxypropylcellulose, nonoxynolhydroxyethylcellulose and cetylhydroxyethylcellulose and nonionic starch derivatives modified with propylene oxide.

5. A multicomponent kit for dyeing keratin fibers, said multicomponent kit consisting of:

a dye carrier mass (A) which is free from dyes and dye precursors;

a granular composition (B) which comprises at least one oxidation dye precursor and/or at least one direct dye and optionally at least one keratin-lightening or bleaching substance; and optionally a suitable oxidizing agent (C)

wherein the granular composition (B) is a dye-containing pellet which is obtained through homogeneous mixing of a starting material comprising at least one natural and/or synthetic dye with a carrier material and subsequent coating with an encapsulation material and in the case of the dye pellet, the encapsulation material is chosen from gum arabic, cellulose derivatives, polyethylene dispersions, polyacrylic acids, polyvinyl alcohols, polyvinylpyrrolidones, polycarbonates, polyesters, polyamides or natural film formers.

6. A method for dyeing or simultaneously dyeing and lightening keratin fibers, said method comprising the steps of:

a) providing a dye carrier mass (A) that is free from dyes and dye precursors;

b) providing a granular composition (B) which comprises at least one oxidation dye precursor and/or at least one direct dye and optionally at least one keratin-lightening or bleaching substance;

c) optionally providing a suitable oxidizing agent (C);

d) mixing said dye-free carrier mass (A) with said granular dye-containing and optionally bleaching agent containing composition (B) and optionally with said oxidizing agent (C) to form a colorant immediately prior to dying the keratin fibers with the colorant; and e) applying the colorant to the keratin fibers wherein the granular composition (B) is a dye-containing pellet which is obtained through homogeneous mixing of a starting material comprising at least one natural and/or synthetic dye with a carrier material and subsequent coating with an encapsulation material or through coating a carrier material with a mixture of at least one natural and/or synthetic dye and at least one encapsulation material.

7. The method as claimed in claim 6, wherein component (A) is used in an amount of from 10 to 120 g, component (B) is used in an amount of from 0.1 to 20 g and component (C) is used in an amount of from 10 to 120 g.

8. The method as claimed in claim 6, wherein the ratio of (A) to (B) is 1000:1 to 2:1 and the ratio of (C) to (A) is 3:1 to 1:3.

9. A method for preparing a colorant for keratin fibers, especially human hair, said method comprising the steps of:

a) providing a dye carrier mass (A) that is free from dyes and dye precursors;

b) providing a granular composition (B) which comprises at least one oxidation dye precursor and/or at least one direct dye and optionally at least one keratin-lightening or bleaching substance;

c) optionally providing a suitable oxidizing agent (C); and d) mixing said dye-free carrier mass (A) with said granular dye-containing and optionally bleaching agent containing composition (B) and optionally with said oxidizing agent (C) to form a colorant immediately prior to dying the keratin fibers with the colorant wherein the granular composition (B) is a dye-containing pellet which is obtained through homogeneous mixing of a starting material comprising at least one natural and/or synthetic dye with a carrier material and subsequent coating with an encapsulation material or through coating a carrier material with a mixture of at least one natural and/or synthetic dye and at least one encapsulation material.

* * * * *